United States Patent
Xu et al.

(10) Patent No.: US 8,175,352 B2
(45) Date of Patent: May 8, 2012

(54) SYSTEM AND METHOD FOR AUTOMATED MAGNETIC RESONANCE SCAN PRESCRIPTION FOR OPTIC NERVES

(75) Inventors: Qing Xu, Nashville, TN (US); Li Zhang, Skillman, NJ (US); Chong Chen, Palo Alto, CA (US)

(73) Assignee: Siemens Aktiengesellschaft, Munich (DE)

( * ) Notice: Subject to any disclaimer, the term of this patent is extended or adjusted under 35 U.S.C. 154(b) by 916 days.

(21) Appl. No.: 12/231,636

(22) Filed: Sep. 4, 2008

(65) Prior Publication Data

US 2009/0080746 A1     Mar. 26, 2009

Related U.S. Application Data

(60) Provisional application No. 60/974,104, filed on Sep. 21, 2007.

(51) Int. Cl.
*G06K 9/00* (2006.01)
(52) U.S. Cl. ....................................................... 382/128
(58) Field of Classification Search ........... 382/128–134
See application file for complete search history.

(56) References Cited

U.S. PATENT DOCUMENTS

| | | | |
|---|---|---|---|
| 5,078,141 A | 1/1992 | Suzuki et al. | |
| 5,652,515 A | 7/1997 | Kondo | |
| 6,138,302 A | 10/2000 | Sashin et al. | |
| 6,396,266 B1 | 5/2002 | Debbins et al. | |
| 6,522,141 B2 | 2/2003 | Debbins et al. | |
| 7,869,663 B2 * | 1/2011 | Buckland et al. | 382/294 |
| 2004/0240753 A1 | 12/2004 | Hu et al. | |
| 2004/0258285 A1 * | 12/2004 | Hansen et al. | 382/128 |
| 2005/0165294 A1 | 7/2005 | Weiss | |
| 2006/0251310 A1 | 11/2006 | Hu et al. | |
| 2008/0044104 A1 * | 2/2008 | Gering | 382/294 |
| 2008/0247622 A1 * | 10/2008 | Aylward et al. | 382/131 |
| 2009/0060308 A1 * | 3/2009 | Dawant et al. | 382/131 |

* cited by examiner

*Primary Examiner* — Clayton E Laballe
*Assistant Examiner* — Dennis Hancock

(57) ABSTRACT

A method and system for automated magnetic resonance (MR) scan prescription is disclosed. A 3D MR scout image is obtained by an initial MR scan. The location of an optic nerve in the scout image is determined by registering a template image to the scout image using a hierarchical series of rigid registrations. The hierarchical series of rigid registrations utilizes a coarse to fine scheme to register regions in the template image to the scout image, starting with the whole template image and finishing with the optic nerve. A diagnostic MR scan is then aligned based on the location of the optic nerve in the scout image, and the diagnostic scan is performed resulting in a high quality diagnostic 3D MR image.

24 Claims, 4 Drawing Sheets

SYSTEM AND METHOD FOR AUTOMATED MAGNETIC RESONANCE SCAN PRESCRIPTION FOR OPTIC NERVES

This application claims the benefit of U.S. Provisional Application No. 60/974,104, filed Sep. 21, 2007, the disclosure of which is herein incorporated by reference.

BACKGROUND OF THE INVENTION

The present invention relates to magnetic resonance scanning, and more particularly, to automated magnetic resonance scan prescription for optic nerves.

Magnetic Resonance (MR) is a well known technique for imaging internal organs of a patient. MR scanners are typically capable of generating cross-sectional images in any plane of the body, including oblique planes. Accordingly, the MR volume data resulting from MR scans can have many possible orientations. In MR scanning, planning is needed in order to determine the orientation and position of the scanning volumes. In a typical MR brain scan process, an MR operator first acquires scout/localizer images by a short time sequence. The operator then manually plans a diagnostic scan from the scout images. The diagnostic scan is an MR scan that results in higher quality MR images than the scout images, such as high-resolution 3D MR images. The plan for the position and orientation of the diagnostic scan is referred to the prescription. The operator can plan diagnostic scans from the scout images using anatomic landmarks. However, different hospitals, departments, and operators many use different anatomic landmarks to plan the scanning. Even when the same anatomic landmarks are used, the scanning can be executed inconsistently, due to inter- or intra-operator variation. This can cause variations in the position and orientation of various MR scans, resulting in inconsistent anatomy display in diagnostic MR images, which can lead to problems with diagnosis when using MR images generated from MR scans. Thus, an automated and consistent MR scan prescription is desirable in clinical MR scanning applications.

BRIEF SUMMARY OF THE INVENTION

The present invention provides a method and system for automated magnetic resonance (MR) scan prescription based on the optic nerve. Embodiments of the present invention automatically identify a location of the optic nerve in MR scout images and guide a diagnostic MR scan based on the optic nerve location.

In one embodiment of the present invention, an MR scout image is received from an initial MR scan. The location of an optic nerve is then determined in the scout image by registering a template image to the scout image using a hierarchical series of rigid registrations. In order to register the template image to the scout image using the hierarchical series of rigid registrations, a first transformation is calculated to register the whole template image to the scout image. The first transformation is fine-tuned based on anatomical landmarks in the scout image. A second transformation is calculated to register an eyes and fat tissue region in the template image to the scout image transformed by the fine-tuned first transformation. A third transformation is calculated to register a left or right eye and fat tissue region in the template image to the scout image transformed by the fine-tuned first transformation and the second transformation. A fourth transformation is calculated to register a fat tissue region surrounding the optic nerve in the template image to the scout image transformed by the fine-tuned first transformation and the second and third transformations. A fifth transformation is calculated to register the optic nerve in the template image to the scout image transformed by the fine-tuned first transformation and the second, third, and fourth transformations. The location of the optic nerve in the template image is transformed by the first, second, third, fourth, and fifth transformations to determine the location of the optic nerve in the scout scan. A diagnostic MR scan is aligned based on the location of the optic nerve in the scout scan.

These and other advantages of the invention will be apparent to those of ordinary skill in the art by reference to the following detailed description and the accompanying drawings.

DETAILED DESCRIPTION OF EXEMPLARY EMBODIMENTS

The present invention relates to automated magnetic resonance (MR) scan prescription based on optic nerve localization. Embodiments of the present invention are described herein to give a visual understanding of the automated MR scan prescription and optic nerve localization methods. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
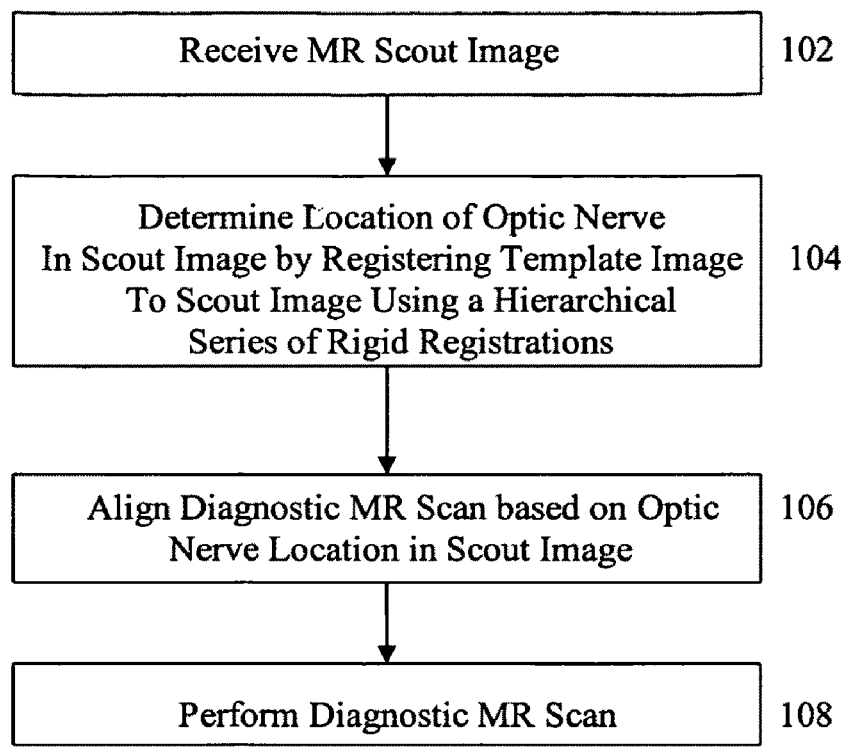
FIG. 1 illustrates a method for automatically determining an MR scan prescription according to an embodiment of the present invention.

FIG. 1 illustrates a method for automatically determining an MR scan prescription according to an embodiment of the present invention. At step 102, an MR scout image is received. The scout image is a 3D MR image (volume) resulting from an initial MR scan of a patient. An MR scout image is typically obtained using a low resolution scan of a patient's brain. The scout image provides initial information about the position and orientation of the patient's brain, which is used to automatically determine a diagnostic scan prescription. The scout image may be received directly from an MR scanning device, or may be loaded, for example, from a memory or storage of a computer system or some other computer readable medium.

At step 104, a location of an optic nerve is determined by registering a template image to the scout image using a hierarchical series of rigid registrations. The hierarchical series of rigid registrations is a multistage image registration based on a combination of optimizing intensity and relevant anatomic landmarks that is used to register the optic nerve in the template image with the optic nerve in the scout scan in order to detect the position and orientation of the optic nerve in the scout scan. The hierarchical series of rigid registrations utilizes a coarse to fine scheme to register regions in the template image to the scout image, starting with the whole template image and finishing with the optic nerve. At each stage in the multistage registration, the accuracy of the registration is increased. The location (position and orientation) of the optic nerve is known in the template image. For example, the optic nerve can be manually located in the template image by an experienced MR operator. Because the position of the optic nerve is known in the template image, the goal of the hierarchical multistage registration is to determine a transformation T that maps the voxels in the template image to the scout image. This is expressed as:

$$x_{scout} = T * x_{template},$$

where $x_{template}$ and $x_{scout}$ are the physical coordinates of voxels of optic nerve in the template image and scout image, respectively.

Figure 2:
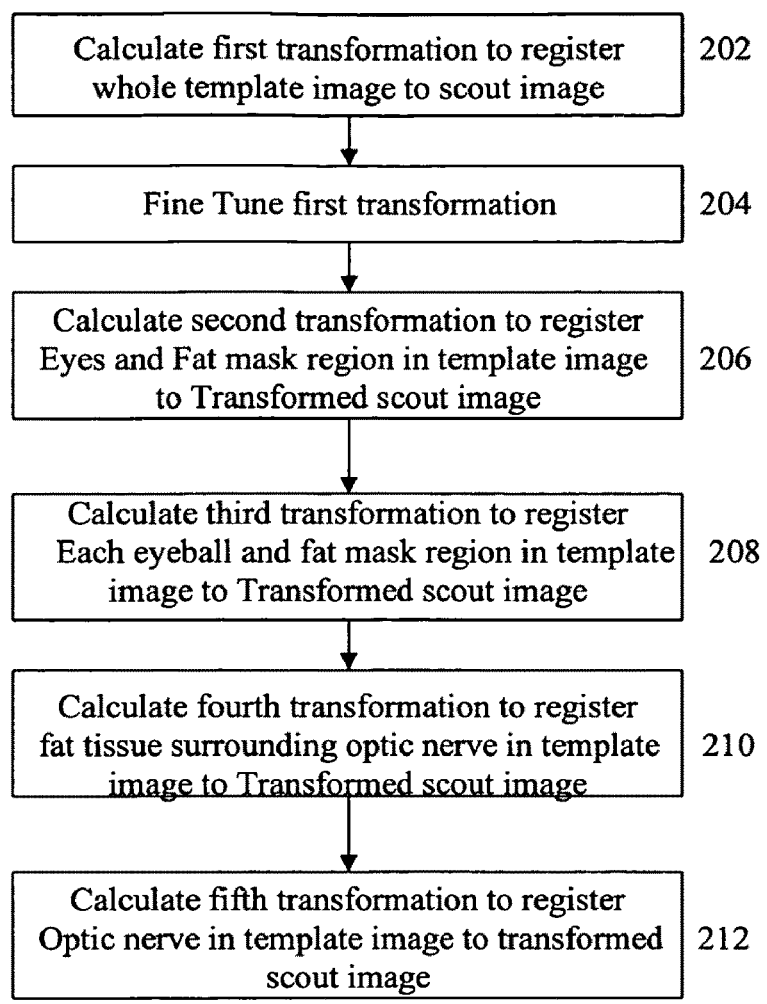
FIG. 2 illustrates a method for determining a location of an optic nerve in a scout image by registering a template image to the scout image using a hierarchical series of rigid registrations according to an embodiment of the present invention.

FIG. 2 illustrates a method for determining a location of an optic nerve in a scout image by registering a template image to the scout image using a hierarchical series of rigid registrations according to an embodiment of the present invention. The method of FIG. 2 can be used to implement step 104 of FIG. 1. The method of FIG. 2 can be used separately to determine the position of the left and right optic nerve. The method of FIG. 2 is described herein as determining the position of the left optic nerve, but it is to be understood that the method can be similarly performed to determine the position of the right optic nerve.

At step 202, a first transformation is calculated to register the whole template image to the scout image. The whole volume of the scout image is aligned to the template image to calculate an approximate transformation $T_{initial}$ that maps any voxel, including the optic nerve, from the template image to the scout image. A rigid 3D registration is used to calculate align the scout image to the template image in order to calculate $T_{initial}$. Formulated as an optimization problem, the registration can be expressed as follows:

$$T_{initial} = \min_{T_{initial}} \sum_{\Omega_{template}} \left( I^{scout}(T_{initial}(\alpha_0, \alpha_1, \alpha_2, \alpha_3, \alpha_4, \alpha_5) * v_{template}) - I^{template}(v_{template}) \right)^2$$

where $\alpha_i$ represents the parameters that determine the transform $T_{initial}$, and $I(v)$ is the intensity value of certain voxel v. $\Omega_{template}$ represents the whole domain of template volume. A rigid versor transformation is used to describe the transformation $T_{initial}$, which can be expressed as follows:

$$\alpha_0 = n_x \sin(\theta/2), \alpha_1 = n_y \sin(\theta/2), \alpha_2 = n_z \sin(\theta/2), \alpha_3 = t_x,$$
$$\alpha_4 = t_y, \alpha_5 = t_z$$

where $[n_x, n_y, n_z]$ is the three components of the rotation axis and $\theta$ is the rotation angle, and $[t_x, t_y, t_z]$ denotes the translation components. A gradient descent method is used for optimizing the mean square intensity difference between the template image and the scout image in order to determine the parameters of $T_{initial}$.

At step 204, the first transformation $T_{initial}$ is fine-tuned based on anatomic landmarks. Due to limitations of rigid registration, $T_{initial}$ may not be accurate enough to provide a reasonable initial transform that accurately maps the optic nerve from the template image to scout image. Several important anatomic landmarks are used to fine-tune the first transformation $T_{initial}$. Lines separating the left and right cerebral hemispheres on coronal and transverse slices of the scout image are extracted to define the mid-sagittal plane (MSP), and $T_{initial}$ is fine-tuned so that it maps any voxel in the MSP of template to the MSP of scout. Then, the crista galli (CG) and the tip of occipital bone (TOB), which are anatomic landmarks in sagittal slices of the scout image, are detected, and $T_{initial}$ is fine-tuned so that it maps CG and TOB of the template image to the CG and TOB of the scout image and as a result, any line parallel to CG-TOB line of template is mapped to a line parallel to the CG-TOB line of the scout image. Accordingly, the center of CG-TOB determines the translation and the CG-TOB line determines the third rotation angle. The CG is used as a landmark for fine-tuning $T_{initial}$, since the location of CG is very relevant to that of the eyeball. After this fine tuning step, $T_{initial}$ is referred to herein as $T_{initial\_fine}$.

At step 206, a second transformation is calculated to register an eyes and fat mask region of the template image to the transformed scout image. The original scout volume is transformed to the transformed scout volume by applying the fine-tuned first transformation $T_{initial\_fine}$. Since the transformed scout image is in a space more similar to the template volume space, the rigid registration used to calculate the second transformation is performed on the transformed scout image. The eyeballs and fat behind them are labeled on the template image manually, and corresponding binary masks are saved.

If $T_{initial\_fine}$ is accurate enough, the mask can be directly mapped to the scout volume by an identity transformation. However, since $T_{initial\_fine}$ may not be accurate enough, the second transformation $T_2$ is calculated that maps the volume of the two eyeballs and the surrounding fat tissue in the template image to the transformed scout image. In order to calculate the second transformation $T_2$, a rigid registration is used to minimize the following expression:

$$T_2 = \min_{T2} \sum_{\Omega_{t2}} (I^{new\_scout}(T_2 * v_{template}) - I^{template}(v_{template}))^2$$

where $\Omega_2$ denotes to the domain of eyeballs and surrounding fat mask in the template image, and $I^{new\_scout}$ represents the intensity value of the $T_{initial\_fine}$ fine transformed scout image.

At step 208, a third transformation is calculated to register each eyeball and fat mask in the template image to the transformed scout image. In order to provide a more accurate result, the registration is further performed on each eyeball (left and right) and the surrounding scout tissue separately. A rigid registration is used to calculate the third transformation, which registers the eyeball and surrounding fat tissue of the template image to the scout image transformed by $T_{initial\_fine}$ and the second transformation $T_2$. The third transformation can be calculated for the left eyeball using a rigid registration as follows:

$$T_{3left} = \min_{T_{3left}} \sum_{\Omega_3} (I^{new\_scout}(T_{3left} T_2 * v_{template}) - I^{template}(v_{template}))^2$$

where $\Omega_{3left}$ denotes to the domain of left eyeball and fat mask in the template image. A similar registration is applied to right eyeball and surrounding fat tissue.

At step 210, a fourth transformation is calculated to register the fat tissue surrounding the optic nerve in the template image to the transformed scout image. Using a coarse to fine scheme, the fat tissue surrounding the optic nerve in the template image is aligned to the scout image separately for the left and right sides. A rigid registration is used to calculate the fourth transformation, which registers the fat tissue surrounding the optic nerve in the template image to the scout image transformed by $T_{initial\_fine}$ and the second and third transformations $T_2$ and $T_3$. The fourth transformation can be calculated for the left fat tissue using a rigid registration as follows:

$$T_{4left} = \min_{T_{4left}} \sum_{\Omega_{4left}} (I^{new\_scout}(T_{4left}T_{3left}T_2 * v_{template}) - I^{template}(v_{template}))^2$$

where $\Omega_{4left}$ denotes the domain of left fat tissue mask surrounding the left optic nerve in the template image. A similar registration is applied to right fat tissue mask surrounding the right optic nerve.

At step 212, a fifth transformation is calculated to register the optic nerve in the template image to the transformed scout image. The optic nerve on the left and right sides are registered to the transformed scout image separately. A rigid registration is used to calculate the fifth transformation, which registers the optic nerve in the template image to the scout image transformed by $T_{initial\_fine}$ fine and the second, third, and fourth transformations $T_2$, $T_3$, and $T_4$. The fifth transformation can be calculated for the left optic nerve using a rigid registration as follows:

$$T_{5left} = \min_{T_{5left}} \sum_{\Omega_{5left}} (I^{new\_scout}(T_{5left}T_{4left}T_{3left}T_2 * v_{template}) - I^{template}(v_{template}))^2$$

where $\Omega_{5left}$ denotes the domain of the left optic nerve in the template image. A similar registration is applied to the right optic nerve to register the right optic nerve in the template image to the transformed scout image.

The location of the optic nerve is determined by the calculated transformations. For example, once the first, second, third, fourth, and fifth transformations are calculated using a series of rigid registrations, the location of the left optic nerve in the scout image is determined as follows:

$$x_{scout} = T_{5left}T_{4left}T_{3left}T_2T_{initial\_fine} * x_{template}$$

where $x_{template}$ and $x_{scout}$ are the physical coordinates of voxels of the optic nerve for template and scout images, respectively. The location of the right optic nerve in the scout image is similarly determined.

Figure 3:
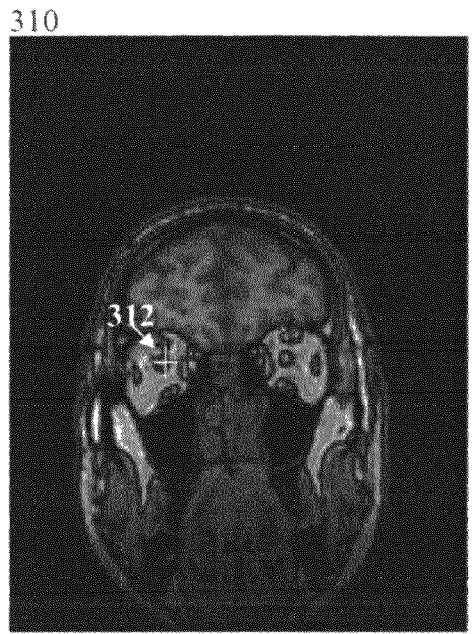
FIG. 3 illustrates exemplary optic nerve location results determined using the method of FIG. 2.
Figure 3:
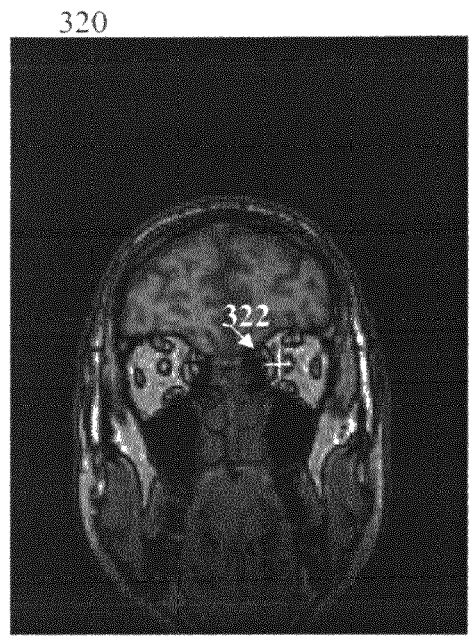

FIG. 3 illustrates exemplary optic nerve location results determined using the method of FIG. 2. As illustrated in FIG. 3, image 310 is a coronal slice of a scout image showing the location of the left optic nerve 312, and image 320 is the same coronal slice showing the location of the right optic nerve 322. The optic nerve can be marked as a series of 2D disks in the template volume, and the left and right optic nerve locations are transformed to the scout image (310 and 320) to give the right and left optic nerve locations 312 and 322 in the scout image (310 and 320).

Returning to FIG. 1, at step 106, the diagnostic MR scan is aligned based on the optic nerve location in the scout image. The diagnostic scan can be aligned to either the left or right optic nerve, or separate diagnostic scans can be performed along each the left and right optic nerves. The diagnostic scan can be aligned such that the coronal plane is perpendicular to the optic nerve, and the sagittal and transverse planes pass through the centerline of the optic nerve. As is well known, the coronal plane separates front and back sides of the image, the sagittal plane separates left and right sides of the image, and the transverse plane separates top and bottom sides of the image.

At step 108, the diagnostic scan is performed using the alignment based on the optic nerve location. As described above, separate diagnostic scans can be guided based on the locations of the left and right optic nerves. Accordingly, each coronal slice is perpendicular to the optic nerve, each sagittal slice is parallel to the optic nerve, and each transverse slice is parallel to the optic nerve. The diagnostic scan results in a high resolution 3D MR volume that can be used for medical diagnosis.

Figure 4:
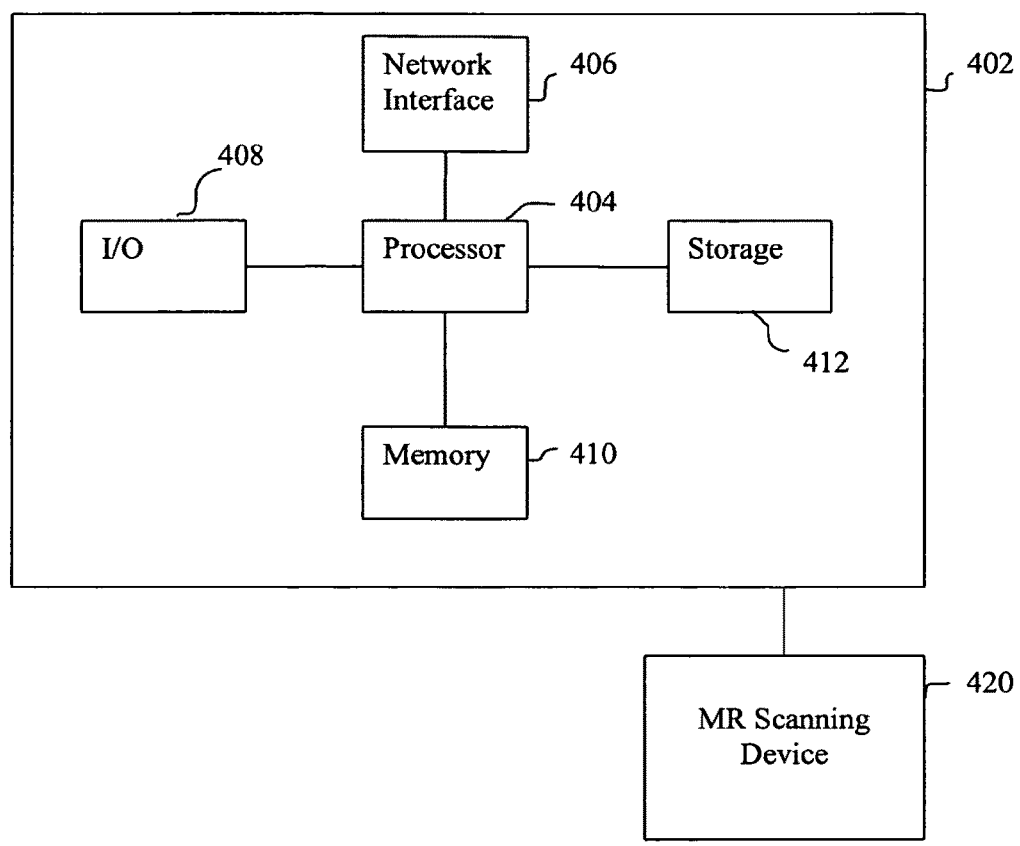
FIG. 4 is a high level block diagram of a computer capable of implementing the present invention.

The above-described methods for determining an MR scan prescription and determining a location of an optic nerve in an MR scout image can be implemented on a computer using well-known computer processors, memory units, storage devices, computer software, and other components. A high level block diagram of such a computer is illustrated in FIG. 4. Computer 402 contains a processor 404 which controls the overall operation of the computer 402 by executing computer program instructions which define such operation. The computer program instructions may be stored in a storage device 412 or other computer readable medium (e.g., magnetic disk, CD ROM, etc.) and loaded into memory 410 when execution of the computer program instructions is desired. Thus, applications for performing the above the method steps of FIGS. 1 and 2 can be defined by the computer program instructions stored in the memory 410 and/or storage 412 and controlled by the processor 404 executing the computer program instructions. Furthermore, image data corresponding to MR brain images, including low-resolution scout images, high-resolution diagnostic images, and template images can be stored in the memory 410 and/or the storage 412. An MR scanning device 420 which generate MR images can be connected to the computer 402 to input MR images to the computer 402. It is possible to implement the MR scanning device and the computer 402 as one device. It is also possible the MR scanning device 420 and the computer 402 communicate wirelessly through a network. The computer 402 also includes one or more network interfaces 406 for communicating with other devices via a network. The computer 402 also includes other input/output devices 408 that enable user interaction with the computer 402 (e.g., display, keyboard, mouse, speakers, buttons, etc.) One skilled in the art will recognize that an implementation of an actual computer could contain other components as well, and that FIG. 4 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:
1. A method, comprising:
receiving a 3D magnetic resonance (MR) scout image; and determining a location of an optic nerve in the scout image by registering a template image to the scout image using a hierarchical series of rigid registrations.

2. The method of claim 1, further comprising:
aligning a diagnostic MR scan based on the location of the optic nerve in the scout image.

3. The method of claim 2, wherein a coronal plane of the diagnostic MR scan is perpendicular to the optic nerve, sagittal plane and transverse planes are parallel to the optic nerve, and at least one sagittal plane and at least one transverse plane passes through the centerline of the optic nerve.

4. The method of claim 1, wherein said step of determining a location of an optic nerve in the scout image comprises:
calculating a first transformation to register a whole volume of the template image to the scout image;
fine-tuning the first transformation based on anatomic landmarks in the scout image;
calculating a second transformation to register eyes and surrounding fat tissue in the template image to the scout image transformed by the fine-tuned first transformation;
calculating a third transformation to register an eyeball and surrounding fat region in the template image to the scout image transformed by the fine-tuned first transformation and the second transformation;
calculating a fourth transformation to register a fat tissue region surrounding the optic nerve in the template image to the scout image transformed by the fine-tune first transformation and the second and third transformations; and
calculating a fifth transformation to register the optic nerve in the template image to the scout image transformed by the fine-tuned first transformation and the second, third, and fourth transformations.

5. The method of claim 4, wherein said step of determining a location of an optic nerve in the scout image further comprises:
determining the location of the optic nerve in the scout image by transforming the location of the optic nerve in the template image using the fine-tuned first transformation, and the second, third, fourth, and fifth transformations.

6. The method of claim 4, wherein said step of fine-tuning the first transformation based on anatomic landmarks in the scout image comprises:
defining a mid-sagittal plane (MSP) in the scout image by extracting lines separating left and right cerebral hemispheres in coronal and transversal slices of the scout image;
fine-tuning the first transformation to map all voxels in the MSP of the template image to the MSP of the scout image;
detecting a crista galli (CG) and a tip of an occipital bone (TOB) in the scout image; and
fine-tuning the first transformation to map the CG and TOB of the template image to the CG and TOB of the scout image such that any line parallel to a CG-OB line in the template image is mapped to a line parallel to the CG-OB line in the scout image.

7. The method of claim 1, wherein said step of determining a location of an optic nerve in the scout image comprises:
separately determining a location of a left optic nerve and a location of a right optic nerve in the scout image.

8. The method of claim 7, further comprising:
guiding a first diagnostic MR scan based on the location of the left optic nerve; and
guiding a second diagnostic MR scan based on the location of the right optic nerve.

9. An apparatus, comprising:
means for receiving a 3D magnetic resonance (MR) scout image; and
means for determining a location of an optic nerve in the scout image by registering a template image to the scout image using a hierarchical series of rigid registrations.

10. The apparatus of claim 9, further comprising:
means for performing a diagnostic MR scan aligned based on the location of the optic nerve in the scout image.

11. The apparatus of claim 10, wherein a coronal plane of the diagnostic MR scan is perpendicular to the optic nerve, and sagittal plane and transverse planes pass through the optic nerve.

12. The apparatus of claim 9, wherein said means for determining a location of an optic nerve in the scout image comprises:
means for calculating a first transformation to register a whole volume of the template image to the scout image;
means for fine-tuning the first transformation based on anatomic landmarks in the scout image;
means for calculating a second transformation to register eyes and surrounding fat tissue in the template image to the scout image transformed by the fine-tuned first transformation;
means for calculating a third transformation to register an eyeball and surrounding fat region in the template image to the scout image transformed by the fine-tuned first transformation and the second transformation;
means for calculating a fourth transformation to register a fat tissue region surrounding the optic nerve in the template image to the scout image transformed by the fine-tune first transformation and the second and third transformations; and
means for calculating a fifth transformation to register the optic nerve in the template image to the scout image transformed by the fine-tuned first transformation and the second, third, and fourth transformations.

13. The apparatus of claim 12, wherein said means for determining a location of an optic nerve in the scout image further comprises:
means for transforming the location of the optic nerve in the template image using the fine-tuned first transformation, and the second, third, fourth, and fifth transformations.

14. The apparatus of claim 12, wherein said means for fine-tuning the first transformation based on anatomic landmarks in the scout image comprises:
means for defining a mid-sagittal plane (MSP) in the scout image by extracting lines separating left and right cerebral hemispheres in coronal and transversal slices of the scout image;
means for fine-tuning the first transformation to map all voxels in the MSP of the template image to the MSP of the scout image;
means for detecting a crista galli (CG) and a tip of an occipital bone (TOB) in the scout image; and
means for fine-tuning the first transformation to map the CG and TOB of the template image to the CG and TOB of the scout image such that any line parallel to a CG-OB line in the template image is mapped to a line parallel to the CG-OB line in the scout image.

15. The apparatus of claim 9, wherein said means for determining a location of an optic nerve in the scout image comprises:

means for separately determining a location of a left optic nerve and a location of a right optic nerve in the scout image.

16. The apparatus of claim 15, further comprising:
means for guiding a first diagnostic MR scan based on the location of the left optic nerve and guiding a second diagnostic MR scan based on the location of the right optic nerve.

17. A non-transitory computer readable medium encoded with computer executable instructions, the computer executable instructions defining steps comprising:
receiving a 3D magnetic resonance (MR) scout image; and
determining a location of an optic nerve in the scout image by registering a template image to the scout image using a hierarchical series of rigid registrations.

18. The non-transitory computer readable medium of claim 17, further comprising computer executable instructions defining the step of:
aligning a diagnostic MR scan based on the location of the optic nerve in the scout image.

19. The non-transitory computer readable medium of claim 18, wherein a coronal plane of the diagnostic MR scan is perpendicular to the optic nerve, and sagittal plane and transverse planes pass through the optic nerve.

20. The non-transitory computer readable medium of claim 17, wherein the computer executable instructions defining the step of determining a location of an optic nerve in the scout image comprise computer executable instructions defining the steps of:
calculating a first transformation to register a whole volume of the template image to the scout image;
fine-tuning the first transformation based on anatomic landmarks in the scout image;
calculating a second transformation to register eyes and surrounding fat tissue in the template image to the scout image transformed by the fine-tuned first transformation;
calculating a third transformation to register an eyeball and surrounding fat region in the template image to the scout image transformed by the fine-tuned first transformation and the second transformation;
calculating a fourth transformation to register a fat tissue region surrounding the optic nerve in the template image to the scout image transformed by the fine-tune first transformation and the second and third transformations; and
calculating a fifth transformation to register the optic nerve in the template image to the scout image transformed by the fine-tuned first transformation and the second, third, and fourth transformations.

21. The non-transitory computer readable medium of claim 20, wherein the computer executable instructions defining the step of determining a location of an optic nerve in the scout image further comprise computer executable instructions defining the step of:
determining the location of the optic nerve in the scout image by transforming the location of the optic nerve in the template image using the fine-tuned first transformation, and the second, third, fourth, and fifth transformations.

22. The non-transitory computer readable medium of claim 20, wherein the computer executable instructions defining the step of fine-tuning the first transformation based on anatomic landmarks in the scout image comprise computer executable instructions defining the steps of:
defining a mid-sagittal plane (MSP) in the scout image by extracting lines separating left and right cerebral hemispheres in coronal and transversal slices of the scout image;
fine-tuning the first transformation to map all voxels in the MSP of the template image to the MSP of the scout image;
detecting a crista galli (CG) and a tip of an occipital bone (TOB) in the scout image; and
fine-tuning the first transformation to map the CG and TOB of the template image to the CG and TOB of the scout image such that any line parallel to a CG-OB line in the template image is mapped to a line parallel to the CG-OB line in the scout image.

23. The non-transitory computer readable medium of claim 17, wherein the computer executable instructions defining the step of determining a location of an optic nerve in the scout image comprise computer executable instructions defining the step of:
separately determining a location of a left optic nerve and a location of a right optic nerve in the scout image.

24. The non-transitory computer readable medium of claim 23, further comprising computer executable instructions defining the steps of:
guiding a first diagnostic MR scan based on the location of the left optic nerve; and
guiding a second diagnostic MR scan based on the location of the right optic nerve.

* * * * *